US006661520B1

(12) United States Patent
Lin et al.

(10) Patent No.: US 6,661,520 B1
(45) Date of Patent: Dec. 9, 2003

(54) SENSOR SYSTEM OF SURFACE PLASMON RESONANCE (SPR) AND MEASURING METHOD THEREOF

(75) Inventors: Chu-Wann Lin, Taipei (TW); Chi-Yu Huang, Taipei (TW); Jyh-Perng Chiu, Taipei (TW); Ying-Tsuen Liou, Taipei (TW); Shuen-Chen Shiue, Taipei (TW); Te-Son Kuo, Taipei (TW); Long-Sun Huang, Taipei (TW); Pei-Zen Chang, Taipei (TW); Lung-Jieh Yang, Taipei (TW); Chau-Chung Wu, Taipei (TW); Shiming Lin, Taipei (TW); Chih-Kung Lee, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 10/153,459

(22) Filed: May 22, 2002

(30) Foreign Application Priority Data

Dec. 21, 2001 (TW) ........................................ 90131926 A

(51) Int. Cl.⁷ ............................................... G01N 21/55
(52) U.S. Cl. ........................................ 356/445; 356/448
(58) Field of Search .............................. 356/445–448, 356/135, 136

(56) References Cited

U.S. PATENT DOCUMENTS

| 5,351,127 | A | * | 9/1994 | King et al. ................. 356/445 |
| 5,804,453 | A | * | 9/1998 | Chen .......................... 436/518 |
| 6,100,991 | A | * | 8/2000 | Challener ................... 356/445 |
| 6,239,876 | B1 | * | 5/2001 | Brandenberg ............... 356/451 |
| 6,268,125 | B1 | * | 7/2001 | Perkins .......................... 435/5 |
| 6,507,402 | B2 | * | 1/2003 | Negami et al. ............. 356/445 |

* cited by examiner

Primary Examiner—Michael P. Stafira
(74) Attorney, Agent, or Firm—Volpe and Koenig, P.C.

(57) ABSTRACT

A sensor system of a surface plasmon resonance (SPR) for analyzing a characteristic of a substance and the measuring method thereof are provided. The system includes an optical device for generating a first light beam and a second light beam in sequence; a sensor device for respectively generating a first plasmon wave and a second plasmon wave in response to an optical characteristic change of the first light beam and the second light beam with respective to the substance, in which a resonance is generated from the first plasmon wave and the second plasmon wave respectively generating a first reflective signal and a second reflective signal; and a measuring device for measuring spectra of the first reflective signal and the second reflective signal and obtaining the measured value which is substituted into an operational formula to calculate a reference value used for analyzing the characteristic of the substance.

23 Claims, 13 Drawing Sheets

SENSOR SYSTEM OF SURFACE PLASMON RESONANCE (SPR) AND MEASURING METHOD THEREOF

FIELD OF THE INVENTION

The present invention is related to a sensor system and a measuring method thereof, and more particularly, to a sensor system of a surface plasmon resonance (SPR) for analyzing a characteristic of a substance and a measuring method thereof.

BACKGROUND OF THE INVENTION

At present, the biological chip is developing vigorously in the academic community, the government, and the private institute in many countries. In respect of DNA chips, many technologies are getting on for maturation, such as the DNA combination analysis, the DNA sequencing, the DNA quantification analysis, the capillary electrophoresis separation detection, the nucleic acid magnification, and the parallel gene expression analysis. Meantime, a series of analyzing methods are derived from these technologies, for instance, the cell separation, the cellular immunity analysis, and the high throughput screening combined with combinatorial chemistry for the first screening of new medicine research. In respect of material, except processing the chip by using the silicon, the plastic molding technology and the plastic body are beginning to be used for processing the biological chip. Nowadays, the three steps of sample handling, chemical reaction, and detection have been integrated partially. Only that the complete integration needs more time, but not so far to get it accomplished. One thing we should pay attention is that the development of biological chip still focuses on the application of DNA chips so far. A series of technologies and products have been developed in the light of the detection requirements for DNA, such as the DNA rapid detection analyzing technology and the product thereof, DNA replication and the segment analyzing technology and the product thereof, and the integrated DNA analyzing system. However, in the aspect of protein chip research, it has not been either largely invested or accomplished. Therefore, a wide research space and the opportunities are left and very suitable as a purpose of biotechnology industry development.

In the present protein research, there is a field called proteomics. This field emphasizes on how to proceed the research at the proteinic level of receptor and hormone in large scale so that the important function, such as the disease mechanism, the cellular operation mechanism, and the cellular net work signal, can be fully understood. These work will offer positive assistance for the development of new medicine, especially the medicine related to protein action within a cell. At present, the choke point of these work is the large consuming of manpower and time. For example, it needs continuous work for 1–8 hours in average, and 1000 protein molecules are required at least for the detection and the analysis. From this, it is not difficult to tell the difficulties and the wide range of this job. It can hardly be accomplished in a short term by the present technology. Hence, a system of protein biomedical chip established by the Micro-Electro-Mechanical System (MEMS) is needed for proceeding the research contributive to the protein level research including the protein structure optimum. Hoping that there will be breakthrough in the direction of medicine designing, medicine screening, new receptor, molecular structure, and intelligent macromolecule element.

At present, a brand-new technology has been provided to this field because of the maturation of the semi-conductor manufacturing technology. A further development for the sensor system has been provided by the Micro-Electro-Mechanical System (MEMS). In addition, the potential in biomedical detection provides a wide market for the Micro-Electro-Mechanical System. Presently, the product, which combines the technologies from different fields including semi-conductor technology, molecular biology, macromolecule material, artificial intelligence, and system integration, has been entered clinical trial from lab experiment. Among the researches full of new ideas, the microarray technology combined with genetic engineering has been applied to the research of gene chips. Many achievements have been made right now and reached the commercialized state. Take $\mu$ Total Analytic System ($\mu$TAS) in the microarray development at the moment as an example, 100–1000 dots within 1 $\mu m^2$ workable for detection. By cooperating with the $\mu$ capillary electrophoresis, the sample can be fast loaded automatically by the manipulator system, so that the separation length is decreased within 5 cm and the separation can be finished within 1 second. If parallel processing is cooperated as well, then the requirements of distant detection and immediate analysis in medicine development are able to rapidly achieved. At present application of protein chips, the detection and analysis of 1024 samples containing lesser than 500 ng can be finished within 3 hours. After the genomic project is claimed finished, the need for the detection of protein function keeps growing and every country is widely developing the protein chip.

The surface plasmon resonance (SPR) phenomenon is an optical method being widely applied to detect the properties of surfaces and interfaces. It is first discovered by physicists and applied to study the properties of metals and dielectric thin films. Afterwards, chemists applied it to study metal/solution interface and Langmuir-Blodgett (LB) thin film. The surface plasmon resonance (SPR) device can display immediate and highly-sensitive detection of biological mutual interaction. It is therefore widely applied to biochemistry research. The surface plasmon can be excited in metal or semi-conductor interface by light energy, electricity energy, mechanical energy, and chemistry energy. The effect of plasmon excitation can be detected by the reflective intensity change when the light incident angle or the wavelength change. However, both the light incident angle and the incident wavelength can only be analyzed two-dimensionally. As to three-dimensional analysis, it is still under researching process and the design mostly focuses on thickness detection. So far, there is no report related to the design with the function for detecting uneven depth, especially the design with the function for detecting different depth of biological molecule which is attached on the chip. It is just the characteristic of the present invention which will be described below.

SUMMARY OF THE INVENTION

It is an object of the present invention to provide a protein chip which can analyze biological molecule immediately.

It is another object of the present invention to provide a biological detection chip which detects sample three-dimensionally by surface plasmon resonance (SPR).

It is another object of the present invention to provide a sensor system of a surface plasmon resonance (SPR) for analyzing a characteristic of a substance, wherein the differences of the penetrated depth of samples are measured and analyzed by the spectrograph analyzer within the wavelength range of both visible light and near infrared light.

According to the present invention, a sensor system of a surface plasmon resonance (SPR) for analyzing a characteristic of a substance, comprises: an optical device for generating a first light beam and a second light beam in sequence; a sensor device mounted between a first dielectric layer and a second dielectric layer for respectively generating a first plasmon wave and a second plasmon wave in response to an optical characteristic change of the first light beam and the second light beam with respective to the substance, wherein the substance is disposed between the sensor device and the second dielectric layer, and a resonance is generated from the first plasmon wave and the second plasmon wave respectively generating a first reflective signal and a second reflective signal in response to a refractive index difference between the first dielectric layer and the second dielectric layer; and a measuring device for measuring spectra of the first reflective signal and the second reflective signal and obtaining a measured value, wherein the measured value is substituted into an operational formula to calculate a reference value used for analyzing the characteristic of the substance.

In accordance with the present invention, the substance is a biological molecule.

Preferably, the substance has a penetrated depth ranged from 1–2500 nm.

Preferably, the first light beam and the second light beam have different wavelengths.

Preferably, the optical device further comprises: a light source for generating the first light beam and the second light beam; a polarizer for polarizing the first light beam and the second light beam and generating a polarized first light beam and a polarized second light beam; plural lens for focusing the polarized first light beam and the polarized second light beam inside an optical fiber so as to allow the polarized first light beam and the polarized second light beam to enter the optical fiber and travel therethrough; and a splitter connecting the optical fiber and a spectrometer, wherein the spectrometer is used for analyzing a spectrum change of the first reflective signal and the second reflective signal generated upon the resonance.

Preferably, the first light beam and the second light beam are respectively visible light and near infrared light, wherein the visible light has a wavelength ranged from 400–700 nm and the near infrared light has a wavelength ranged from 700–1500 nm.

Preferably, the sensor device is one of a surface plasmon resonance (SPR) optical fiber sensor and a surface plasmon resonance (SPR) chip sensor.

Preferably, the sensor device is one of a surface plasmon resonance (SPR) optical fiber sensor and a surface plasmon resonance (SPR) chip sensor.

Preferably, the sensor device further comprises: a multi-layer structure; and a coupler for coupling the first light beam and the second light beam to the multi-layer structure.

Preferably, the multi-layer structure further comprises a multimode metal layer, a biomedical linker layer and a biomedical ligand layer in sequence.

Preferably, the multimode metal layer has a thickness ranged from 10–300 nm.

Preferably, the multimode metal layer is composed of plural metal layers with different thicknesses.

Preferably, the multimode metal layer is composed of plural metal layers made of different materials.

Preferably, the substance is attached on the surface of the multimode metal layer.

Preferably, the first light beam and the second light beam are incident upon the second dielectric layer through the first dielectric layer.

Preferably, the first dielectric layer has a refractive index larger than that of the second dielectric layer.

Preferably, the measuring device includes a hardware device and a software device.

Preferably, the hardware device is a spectrometer for measuring the measured value and the software device is a digital signal processing program.

Preferably, the spectra of the first reflective signal and the second reflective signal have the measured value including a site, a width, and a penetrating depth.

Preferably, the operational formula is a specific equation using a least square curvilinearly coordinating spectra of the first reflective signal and the second reflective signal to obtain the reference value.

Preferably, the reference value includes a refractive index, a light-eliminating factor, and a thickness.

According to another aspect of the present invention, a measuring method of a surface plasmon resonance (SPR) system for analyzing a characteristic of a substance, comprising steps of: (a) providing a first light beam and a second light beam; (b) providing a sensor device for respectively generating a first plasmon wave and a second plasmon wave in response to an optical characteristic change of the first light beam and the second light beam with respect to the substance; (c) generating a resonance from the first plasmon wave and the second plasmon wave respectively generating a first reflective signal and a second reflective signal in response to a refractive index difference between a first dielectric layer and a second dielectric layer; and (d) measuring spectra of the first reflective signal and the second reflective signal and obtaining a measured value, wherein the measured value is substituted into an operational formula to calculate a reference value used for analyzing the characteristic of the substance.

In accordance with the present invention, the first light beam and the second light beam are provided from an optical device.

In accordance with the present invention, the measured value is obtained from a spectrometer.

The foregoing and other features and advantages of the present invention will be more clearly understood through the following descriptions with reference to the drawings, wherein:

BRIEF DESCRIPTION OF THE DRAWINGS

FIG. 4(b1) is a diagram illustrating the measuring spectrum of the surface plasmon resonance (SPR) reflective signal in alcohol and glycerine solution, wherein the wavelength falls within the range of visible light according to a preferred embodiment of the present invention;

FIG. 4(a2) is diagram illustrating the measuring spectrum of the surface plasmon resonance (SPR) reflective signal in alcohol and glycerine solution, wherein the wavelength falls within the range of near infrared light according to a preferred embodiment of the present invention;

FIG. 4(b2) is a diagram illustrating the measuring spectrum of the surface plasmon resonance (SPR) reflective signal in deionized water and distilled water, wherein the wavelength falls within the range of near infrared light according to a preferred embodiment of the present invention;

DETAILED DESCRIPTION OF THE PREFERRED EMBODIMENT

Figure 1:
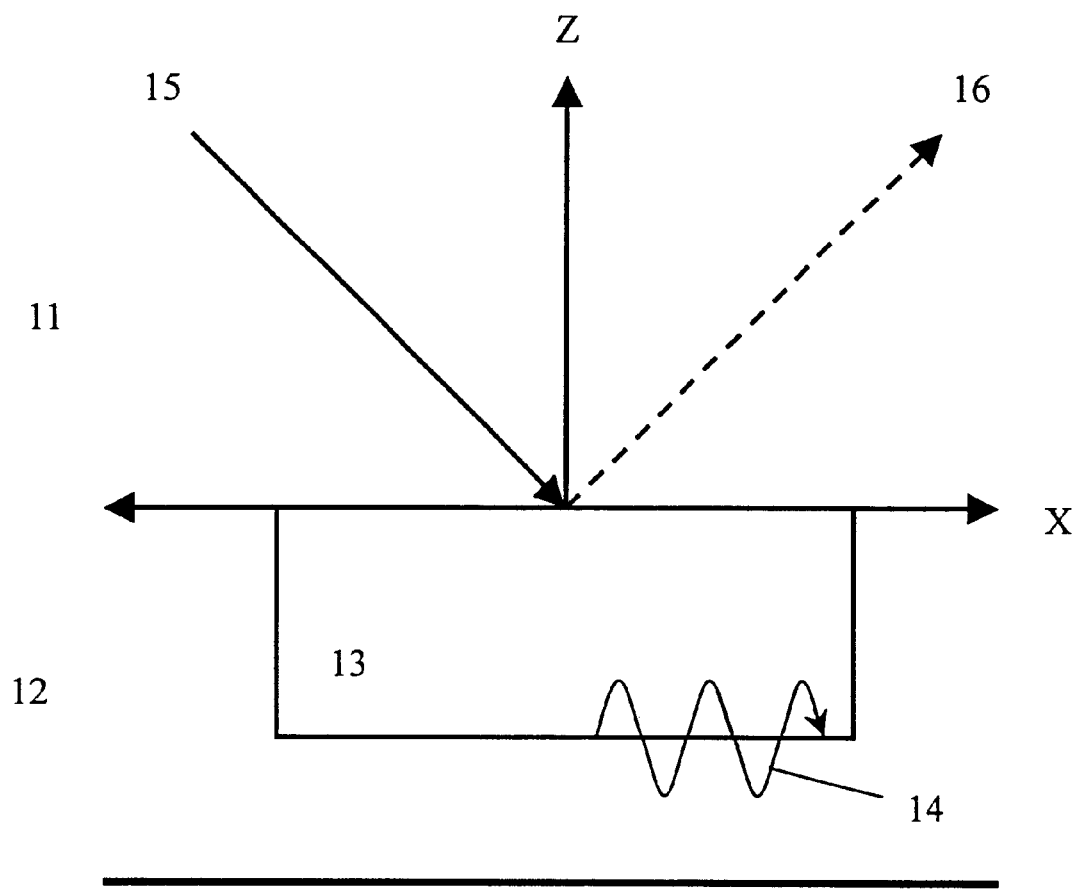
FIG. 1 is a diagram illustrating the excitation phenomenon, in which the surface plasmon is generated from exciting the free electrons in a metal interface by optical coupling.

The present invention will now described more specifically with reference to the following embodiments. Please refer to FIG. 1. The diagram illustrates the excitation phenomenon, in which the surface plasmon is generated from exciting the free electrons in a metal interface by optical coupling. The optical excitation of plasmons is possible only when a proper coupling of light to metal. This can be accomplished by using the attenuated total reflection (ATR) method, which is the measuring method of the present invention. The evanescent waves are used to detect the biomedical and photoelectric sample instead of the light beam itself. This method is that, under the condition of total internal reflection, the incident light 15 is incident upon a second medium 12 from a first medium 11 having a higher refractive index. Under most situations, the light wave will be completely reflected without transferring any energy. Hence, the reflective index of the second medium 12 is 1. However, under the particular situation (when the incident angle or the wavelength is changed), the incident electromagnetic wave will induce the vibration 14 of free electrons in the metal layer 13. The plasmon can enter the second medium 12 through the electromagnetic field which follows the vibration 14 of free electrons to be generated. In the moment, there is energy being transferred in the interface, so the reflective index of the second medium 12 is smaller than 1. It is therefore being called attenuated total reflection (ATR) light 16 and its penetrating distance is decreased exponentially. At a particular incident angle (constant wavelength), or a particular wavelength (constant incident angle), the light wave vector matches the wave vector of the plasmon, fulfilling the resonance conditions for plasmon generation, which is called the surface plasmon resonance (SPR). During the resonance interaction, the energy is transferred from photons to plasmons, so that the effect of plasmon excitation can be observed as a sharp minimum of the reflectance when the angle of light incidence or the wavelength is varied. Thus an internal reflection Spectroscopy (IRS) is defined and called the surface plasmon resonance (SPR) spectrum. The position of resonance wavelength (or angle) and the spectrum shape of the surface plasmon resonance (SPR) are very sensitive to the change of optical properties of a metal thin layer and a dielectric layer (biological molecule) next to the metal surface. According to these properties, the surface plasmon resonance (SPR) is ideally suitable for studying the structural and mass change of a slight dielectric thin layer such as the interaction between a solid thin film and a liquid thin film, the interaction between a liquid thin film and protein, the interaction among whole thin film, periphery, and water-dissolvable protein.

Figure 2:
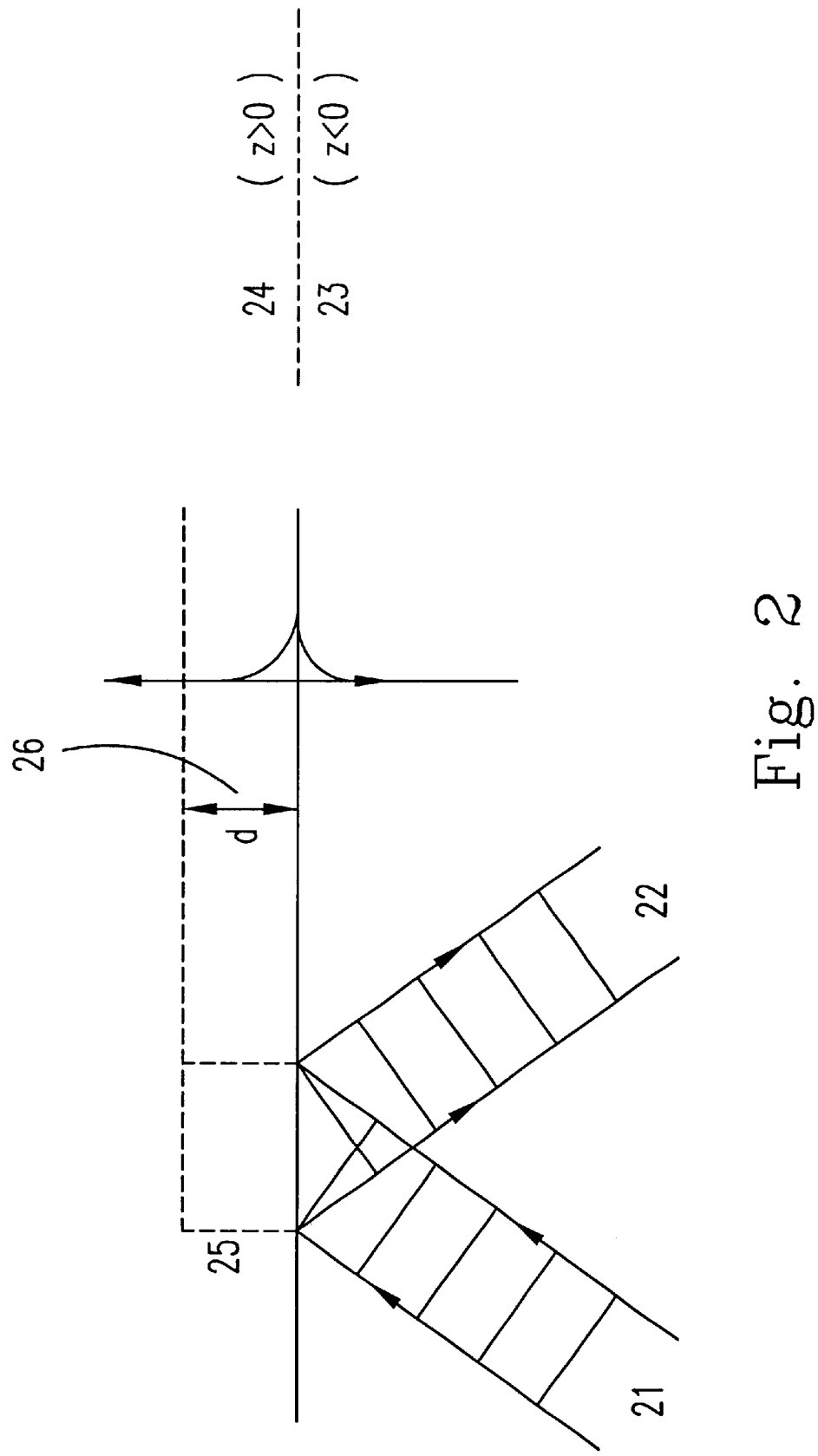
FIG. 2 is a diagram illustrating the measurement of penetrating depth in different biological molecule according to a preferred embodiment of the present invention.

Please refer to FIG. 2. The diagram illustrates the measurement of penetrating depth in different biological molecule according to a preferred embodiment of the present invention. The electromagnetic wave of the incident light 21 induces the vibration of free electrons in the metal layer 23 to penetrate the dielectric layer (biological molecule) 24 next to the metal surface. A penetrating depth 26 is formed in the evanescent field region 25 of the dielectric layer (biological molecule) 24.

Additionally, the measuring method for the depth of different biological molecules is provided as following:

1. When a p-polarized light incident on a X-Z plane: for dielectric layer, Z<0:

$$\overline{H_2} = [0, H_{y2}, 0] e^{i(k_{x2}x + k_{z2}z - \omega t)}$$

$$\overline{E_2} = [E_{x2}, 0, E_{z2}] e^{i(k_{x2}x + k_{z2}z - \omega t)}$$

for metal layer, Z>0:

$$\overline{H_1} = [0, H_{y1}, 0] e^{i(k_{x1}x - k_{z1}z - \omega t)}$$

$$\overline{E_1} = [E_{x1}, 0, E_{z1}] e^{i(k_{x1}x - k_{z1}z - \omega t)}$$

where, $\overline{H_1}$: Magnetic field in metal layer; $\overline{H_2}$: Magnetic field in dielectric layer; $\overline{E_1}$: Electric field in metal layer; $\overline{E_2}$:

Electric field in dielectric layer; $H_{y1}$: Y component of the magnetic field in metal layer; $H_{y2}$: Y component of the magnetic field in dielectric layer; $E_{x1}$: X component of the magnetic field in metal layer; $E_{x2}$: X component of the magnetic field in dielectric layer; $E_{z1}$: Z component of the magnetic field in metal layer; $E_{x2}$: Z component of the magnetic field in dielectric layer; $K_{x1}$: X component of the wave vector in metal layer; $K_{x2}$: X component of the wave vector in dielectric layer; $K_{z1}$: Z component of wave vector in metal layer; $K_{z2}$: Z component of wave vector in dielectric layer; $\omega$: Angular frequency of the incident light.

2. Using the Maxwell's equation, $$\nabla \times \vec{E}_i = \frac{-1}{c}\frac{\partial \vec{H}_i}{\partial t} \quad (1)$$

$$\nabla \times \vec{H}_i = \varepsilon_i \frac{-1}{c}\frac{\partial \vec{E}_i}{\partial t} \quad (2)$$

$$\nabla \cdot \in_i \vec{E}_i = 0 \quad (3)$$

$$\nabla \cdot \vec{H}_i = 0 \quad (4)$$

and the boundary conditions $$E_{x1} = E_{x2} \quad (5)$$

$$H_{y1} = H_{y2} \quad (6)$$

$$\in_1 E_{z1} = \in_2 E_{z2} \quad (7)$$

where $\in_1$: dielectric function in metal layer; $\in_2$: dielectric function in dielectric layer.

From the formula (2)

$$\rightarrow \frac{\partial H_{yi}}{\partial z} = -i\varepsilon_i \frac{\omega}{c} E_{xi} \rightarrow k_{z1} H_{y1} = \frac{\omega}{c}\varepsilon_1 E_{x1} \bigg) k_{z2} H_{y2} = -\frac{\omega}{c}\varepsilon_2 E_{x2} \quad (8)$$

To substitute the formula (8) and formula (6) into formula (5), $$\rightarrow \begin{pmatrix} H_{y1} - H_{y2} = 0 \\ \frac{k_{z1}}{\varepsilon_1}H_{y1} + \frac{k_{z2}}{\varepsilon_2}H_{y2} = 0 \end{pmatrix}$$

and obtain $$k_{zi} = \sqrt{\varepsilon_i\left(\frac{\omega}{c}\right)^2 - k_x^2} \quad (9)$$

$$k_x = \frac{\omega}{c}\sqrt{\frac{\varepsilon_1 \varepsilon_2}{\varepsilon_1 + \varepsilon_2}}$$

From formula (9), $k_z$ is imaginary number, so $k_z = |k_z|i$ $$E = E_0 e^{i(k_{x1}x - k_{z1}z - \omega t)}$$

$$E = E_0 e^{-|k_z|z}$$

The dielectric function of metal is $\in_1 = \in_1' + i\in_1''$
The penetrating depth of dielectric layer (biological-molecule) is $$d_p = \frac{1}{|k_{z2}|} = \left|\frac{\lambda}{2\pi}\sqrt{\frac{\varepsilon_1' + \varepsilon_2}{\varepsilon_2^2}}\right|$$

When the light source used is not a light source with single wavelength, and there are two resonance wavelengths $\lambda_1$ and $\lambda_2$ existed:

$$d_p(\lambda_1) = \left|\frac{\lambda_1}{2\pi}\sqrt{\frac{\varepsilon_1'(\lambda_1) + \varepsilon_2(\lambda_1)}{\varepsilon_2(\lambda_1)^2}}\right|$$

$$d_p(\lambda_2) = \left|\frac{\lambda_2}{2\pi}\sqrt{\frac{\varepsilon_1'(\lambda_2) + \varepsilon_2(\lambda_2)}{\varepsilon_2(\lambda_2)^2}}\right|$$

Figure 3:
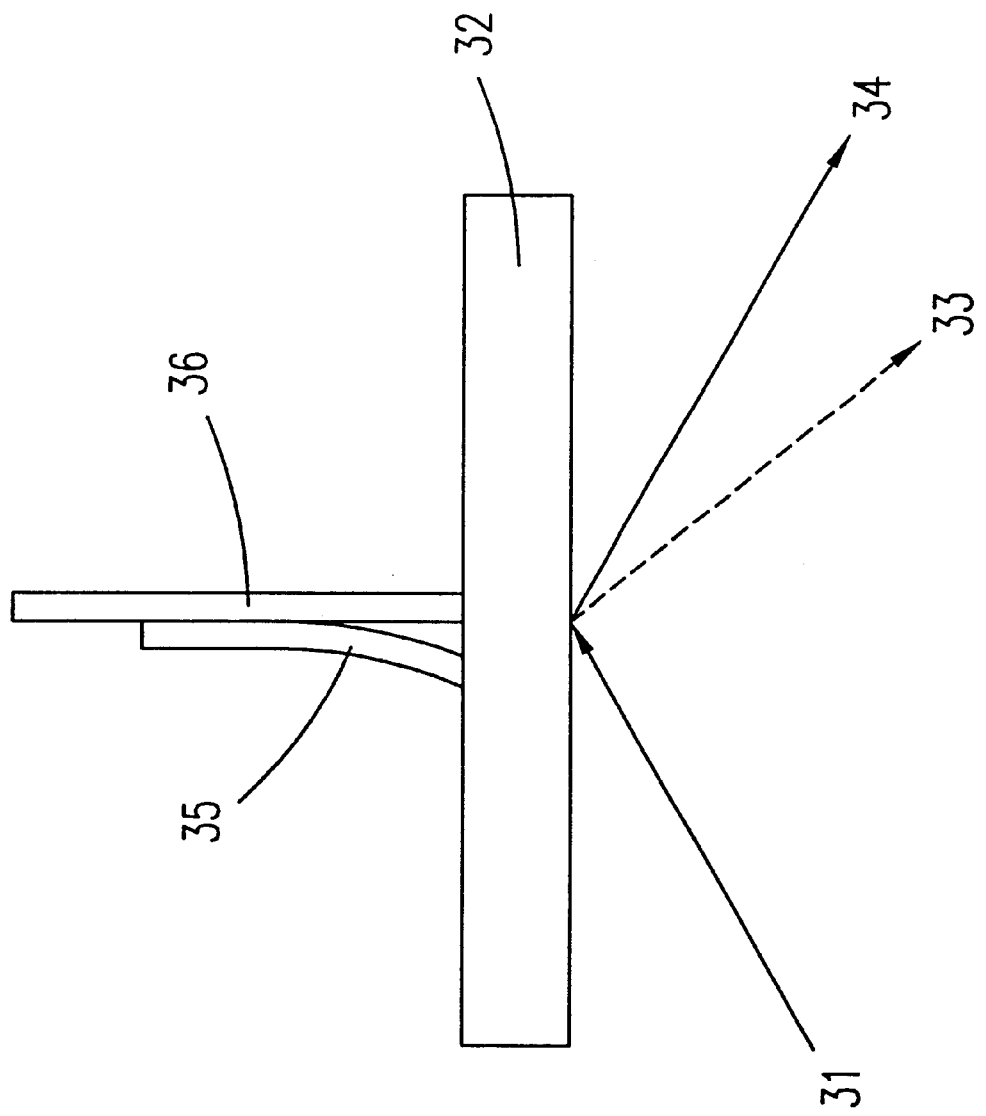
FIG. 3 is a diagram illustrating the mechanism of measuring the depth according to a preferred embodiment of the present invention.

The differences of the biological molecules in different depth are able to be detected in evanescent field with different penetrating depths by using different wavelength and the resonance generated thereof. Please refer to FIG. 3. The diagram illustrates the mechanism of measuring the depth according to a preferred embodiment of the present invention. When the incident light 31 with different wavelengths incidents upon the metal layer 32, the reflective light 33 and 34 will have different reflective angles because of the different penetrating depth 35 and 36. If the penetrating depth is shallower, then the reflective angle will be relatively larger.

Additionally, the surface plasmon generated by optical coupling in the present invention is accomplished by the following formulas:

1. Using a ATR coupler,
the momentum:

$$\frac{\eta\omega}{c} \rightarrow \frac{\eta\omega}{c}\sqrt{\varepsilon_0}$$

$$k_x = \sqrt{\varepsilon_0}\frac{\omega}{c}\sin\theta \quad (\theta: incident\ angle)$$

for a p-polarized light:

Fresnel's coefficients $$r_{ik} = (k_{zi}/\in_i - k_{zk}/\in_k)/(k_{zi}/\in_i + k_{zk}/\in_k)$$

defines: $a = k_{z1} \cdot d_1$ $d_1$: thickness of metal layer $$k_{zi} = \sqrt{\left[\varepsilon_i\left(\frac{\omega}{c}\right)^2 - (k_x^0 + \Delta k_x)^2\right]}$$

$$\Delta k_x = r_{01}e^{2i\alpha} \cdot 2\left(\frac{\omega}{c}\right)\left(\frac{\varepsilon_1 \varepsilon_2}{\varepsilon_1 + \varepsilon_2}\right)^{32}/(\varepsilon_2 - \varepsilon_1)$$

$$r_{01} = (a^2 - i\varepsilon_0^2)/(a^2 + i\varepsilon_0^2),$$

where, $a^2 = -\in_1'(\in_0 - 1) - \in_0$ internal damping:

$$\Gamma_i = k_x''$$

radiation damping:

$$\Gamma_{rad} = Im\{\Delta k_x\}$$

$$k_x = k_z' + Re(\Delta k_z) + i(\Gamma_i + \Gamma_{rad})$$

$$r_{012} = r_{01}\{[k_x - (k_x + \Delta k_x) - i(\Gamma_i - \Gamma_{rad})]/[k_x - (k_x + \Delta k_x) - i(\Gamma_i + \Gamma_{rad})]\}$$

reflective index:

$$R = |r_{012}|^2$$
$$= 1 - (4\Gamma_i \Gamma_{rad} / \{[k_x - \text{Re}\{k_x^0\} + \text{Re}\{\Delta k_x\}]^2 + (\Gamma_i + \Gamma_{rad})^2\})$$

From the above, it is known that, the differences of the dielectric substances are able to be distinguished by the frequency spectrum of the surface plasmon resonance (SPR) since different dielectric layers (biological molecules) have different spectra of the surface plasmon resonance (SPR). The differences of the biological molecules in different depth are able to be distinguished too since the generated resonance wavelength has different penetrating depths and different spectra of the surface plasmon resonance (SPR).

The established system for measuring the reflective signal of surface plasmon resonance (SPR) in the present invention includes several parts: 1. the optical system; 2. the optical fiber sensor of the surface plasmon resonance (SPR); and 3. measuring and analyzing system. The description of these parts is shown below:

1. the optical system: This part includes a light source, polarizers, lens, optical fiber connector, a splitter, and a spectrograph analyzer.

The main purpose of the optical system is to provide an excited light source. After being modulated by optical elements, the light beam will be coupled to the optical fiber sensor of the surface plasmon resonance (SPR) through the light coupling. Finally, the reflective signal will be analyzed by the spectrograph analyzer of the optical fiber and the SPR reflective signal will be shown on the monitor.

(1) The light source: The light source system used here is a light source system with multi-wavelength. Therefore, the multi-wavelength modulation technique is used to excite the SPR resonant peak under different wavelengths.

(2) The polarizers: The polarizer used in the present invention is linear polarizer. The linear polarizer is used to polarize the light beam generated by the light source to a certain direction, so that the polarization thereof will be generated and the light beam will travel toward a certain polarized direction.

(3) The lens: the lens used here is to focus the polarized light inside the coupling optical fiber so as to allow the polarized light to enter the optical fiber and travel therethrough.

(4) The optical fiber connector: The optical fiber connector is an optical fiber communication element, which is used to connect two optical fibers through the optical fiber connector so that the light beam can travel form one optical fiber to another. Therefore, the signal lost caused by the optical fiber connector can be reduced by the optical adhesive.

(5) The splitter: The splitter used here is the one-to-two splitter and the splitting rate is 50/50. In this optical system, a light beam is mainly transmitted into one of the optical fibers, and the another optical fiber of the splitter is connected to spectrograph analyzer for measuring and analyzing the responded signal of SPR reflection.

(6) The spectrograph analyzer: In this system, the measured SPR reflective signal is transmitted into the spectrograph analyzer through the another optical fiber of the splitter. The signal will then be acquired to a computer through data acquisition quantification (DAQ) so that the position of the SPR resonant peak can be judged.

Therefore, the structure of the whole optical system mainly uses a excited light source to generate excited light beam within different ranges of wavelength. Through the action of polarizer, the light beam is polarized to a particular state. The polarized light generated thereof is then coupled into the optical fiber by the focusing of the lens. The light beam is 50/50 split by the one-to-two beamsplitter. The light beam is then transmitted into one of the optical fibers, which is connected to the optical fiber sensor of the surface plasmon resonance (SPR). The light beam is transmitted to the sensor due to the light beam is coupled to the surface of the SPR optical fiber sensor and a phenomenon of the surface plasmon resonance (SPR) is generated. The reflective signal of this phenomenon is transmitted to the polarizer through the optical fiber at the another end of the splitter. After filtering the interfered signal by the selective polarized light of polarizer, the SPR reflective signal is truly transmitted to the spectrograph analyzer. After the signal analyzing by the spectrograph analyzer, the signal is finally acquired to a computer through data acquisition quantification (DAQ) so that the measured SPR reflective signal can be shown.

2. The optical fiber sensor of the surface plasmon resonance (SPR): The optical fiber sensor of surface plasmon resonance (SPR) is the main measuring part in this system. The phenomenon of surface plasmon resonance (SPR) is generated the surface of the SPR optical fiber sensor. The light beam is transmitted to the sensor due to the light coupling to the surface of the SPR optical fiber sensor and a surface plasmon wave (SPW) is therefore generated. The surface plasmon wave (SPW) will generated surface plasmon resonance (SPR) because of the change of the sample's refractive index in the outer environment. This phenomenon can be shown by the SPR optical fiber sensor so that the signal can be reflected into the optical fiber and transmitted to the spectrograph analyzer to be analyzed. Therefore, through the change of the refractive index in the environment, the SPR optical fiber sensor is able to measure the reflective signal by the sensor and truly transmit it to the spectrograph analyzer. This part is the key measuring part, hence the most advance micro electromechanical technology (MEMS) is used to manufacture the optical fiber sensor of surface plasmon resonance (SPR).

3. The measuring and analyzing system: The signal measuring and analyzing system of the present invention can be divided into a hardware device and a software device. The main purpose of this system is to show the reflective resonant peak by analyzing and acquiring the reflective signal by the spectrograph analyzer and the digital signal processing at the distant end so that the information about function can be obtained.

(1) Hardware device: In the aspect of a hardware device, the spectrograph analyzer is used, which has a resolution up to 3 nm. The SPR reflective signal is transmitted from the splitter mirror to the polarizer and the signal will be detected by the spectrograph analyzer after the interfered signal is filtered. An continuous analogy signal will be obtained after analyzing the SPR reflective signal in the spectrograph analyzer by the detection and analyzing of the inner circuit. After the analogy signal is acquired by the data acquisition quantification (DAQ), it will be turned into a digital signal and transmitted into the computer. In order to maintain the signal fidelity at the hardware part, both the resolution of the spectrograph analyzer and the quantification extent of the data acquisition quantification need to be considered to avoid the lost of the reflective signal at this part of the system.

(2) Software device: At the software part, the program of the digital signal processing is wrote to cooperate the acquired reflective signal. The design of the software includes the functions of the sampling time, the filter, and the regression analysis so that the acquired reflective signal can be totally displayed through the technique of the digital signal processing.

Figure 4:
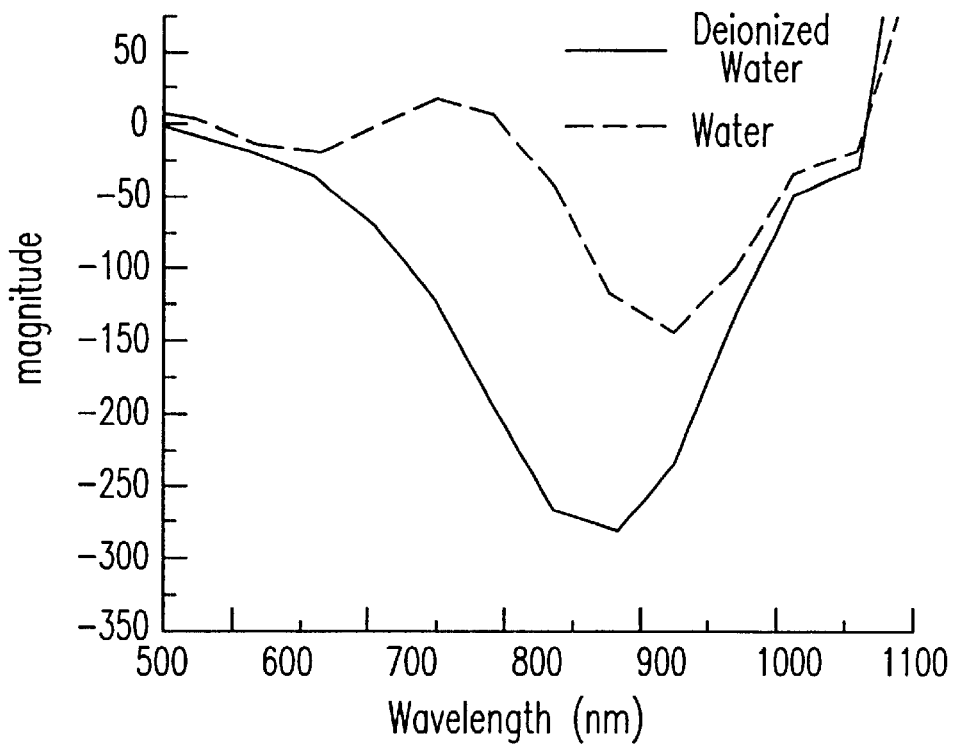
FIG. 4(a1) is a diagram illustrating the measuring spectrum of the surface plasmon resonance (SPR) reflective signal in deionized water and distilled water, wherein the wavelength falls within the range of visible light according to a preferred embodiment of the present invention.
Figure 4:
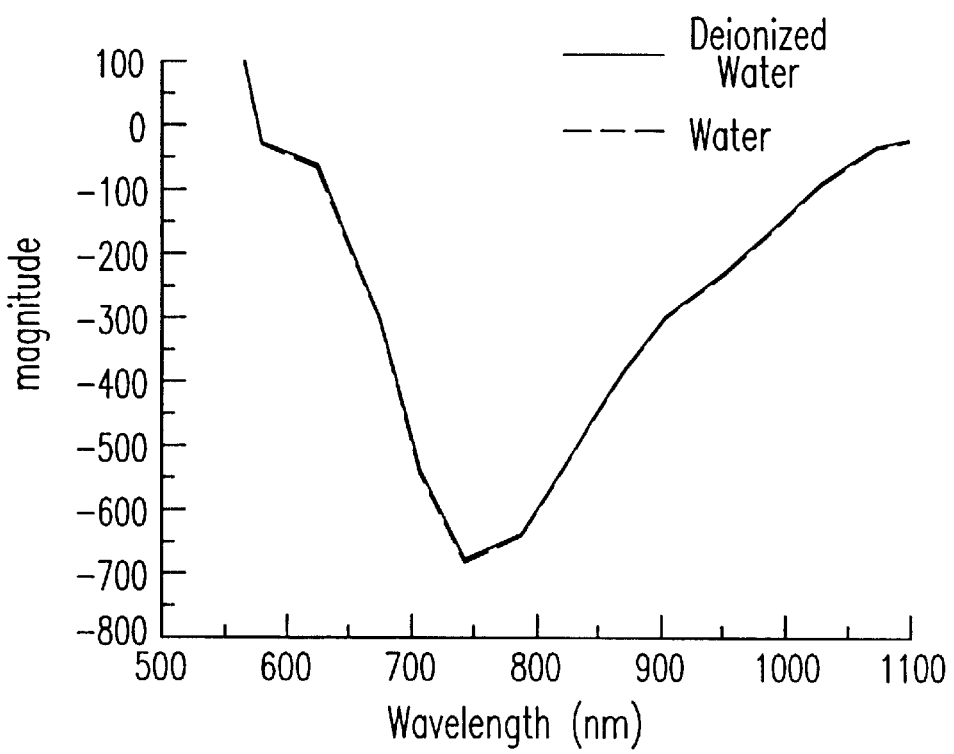
Figure 4:
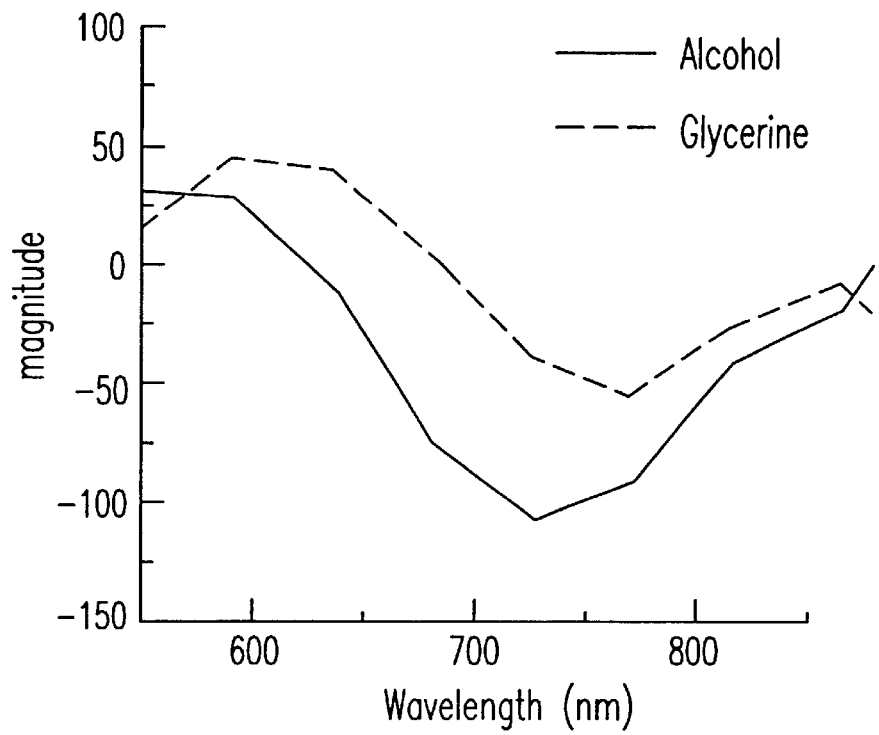
Figure 4:
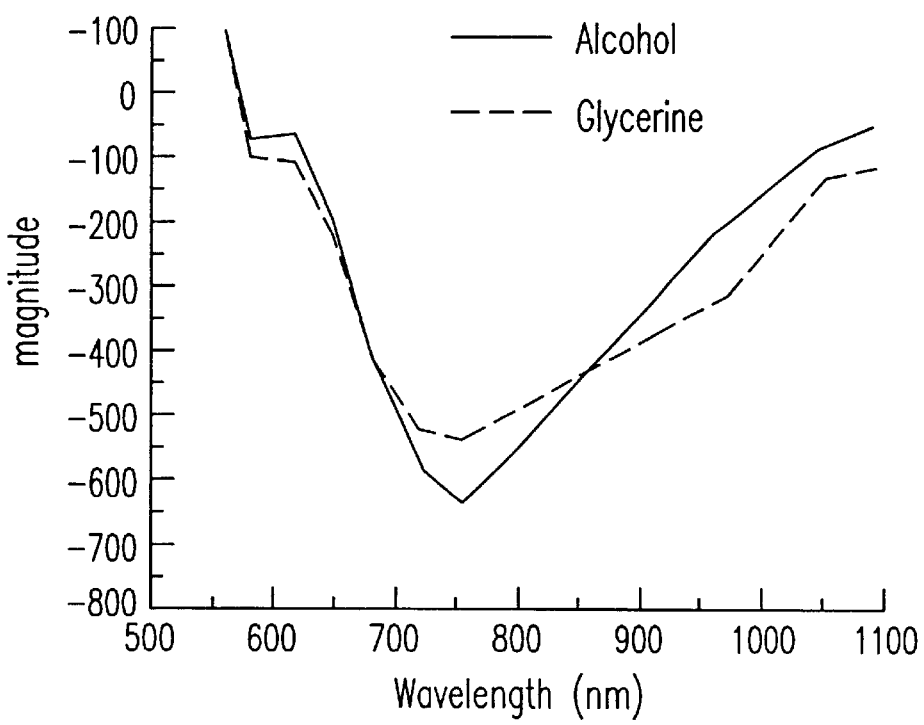

Please refer to FIGS. 4(*a*1), (*b*1), (*a*2), and (*b*2). The diagrams illustrate the measuring spectrum of the surface plasmon resonance (SPR) reflective signal in different solutions, in which the wavelength falls within the range of visible light and near infrared light according to a preferred embodiment of the present invention. The obtained spectra are different because of the change of the refractive index in the environment. The SPR reflective signal is existed in the wavelength range of both visible light and near infrared light. However, from the reflective signal, it can be found that the frequency spectra in the wavelength range of near infrared light is sharper and more obvious than that of visible light. Therefore, it is know that the SPR resonant peak is sharper and more specific in the wavelength range of near infrared light than that of visible light. The position of the SPR resonant peak can be known more accurately without affecting by the outside interfered signal or losing the signal fidelity. In other words, the excited light source has a better sharpness and accuracy in the wavelength range of near infrared light than that of visible light, which is also the main point of the present invention.

Figure 5A:
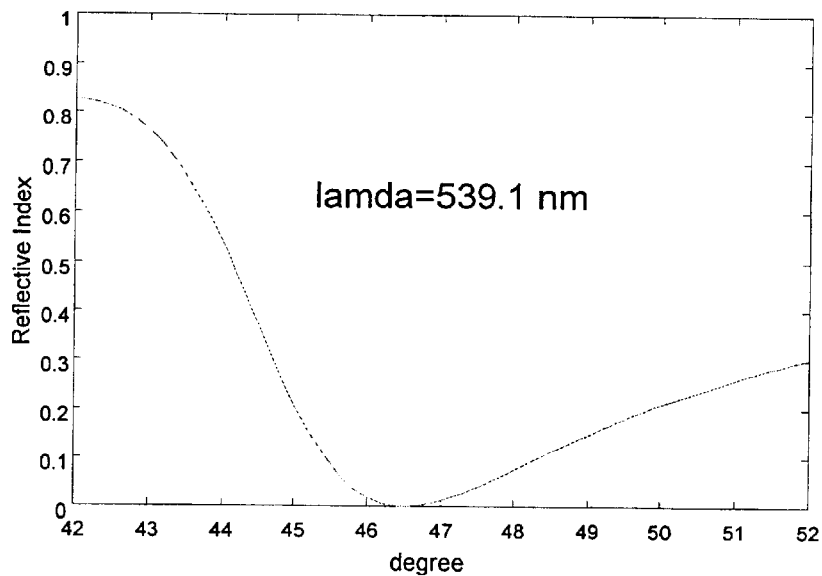
FIG. 5(a) is a diagram illustrating the frequency spectrum of the surface plasmon resonance (SPR) in the air within the wavelength range of visible light according to a preferred embodiment of the present invention.
Figure 5B:
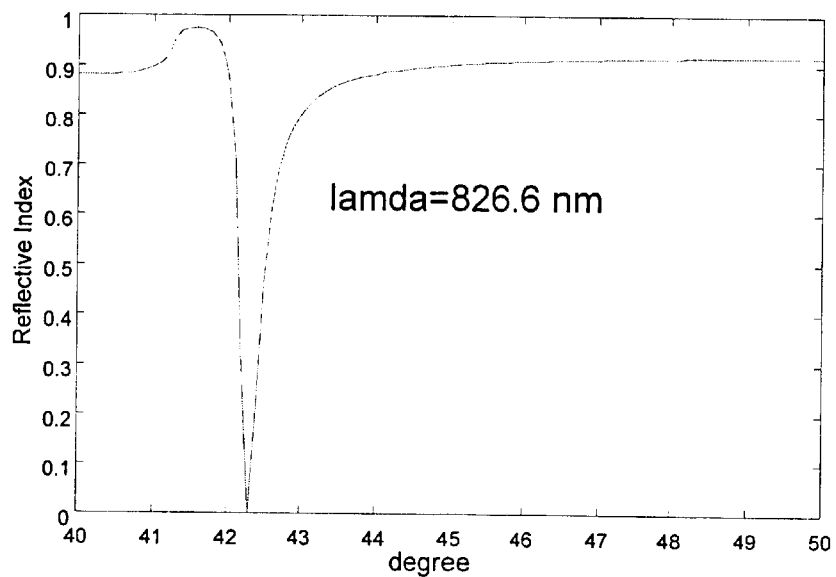
FIG. 5(b) is a diagram illustrating the frequency spectrum of the surface plasmon resonance (SPR) in the air within the wavelength range of near infrared light according to a preferred embodiment of the present invention.

Please refer to FIGS. 5(*a*) and (*b*). The diagrams illustrate the frequency spectrum of surface plasmon resonance (SPR) in the air within the wavelength range of visible light and near infrared light according to a preferred embodiment of the present invention. It can be seen clearly that, the SPR spectrum in the wavelength range of near infrared light is thinner and longer than that of visible light. Therefore, when the SPR resonance position changes, it gets easier to recognize the spectrum in the wavelength range of near infrared light, which helps the more exquisite and accurate detection of the biological molecule.

Figure 6:
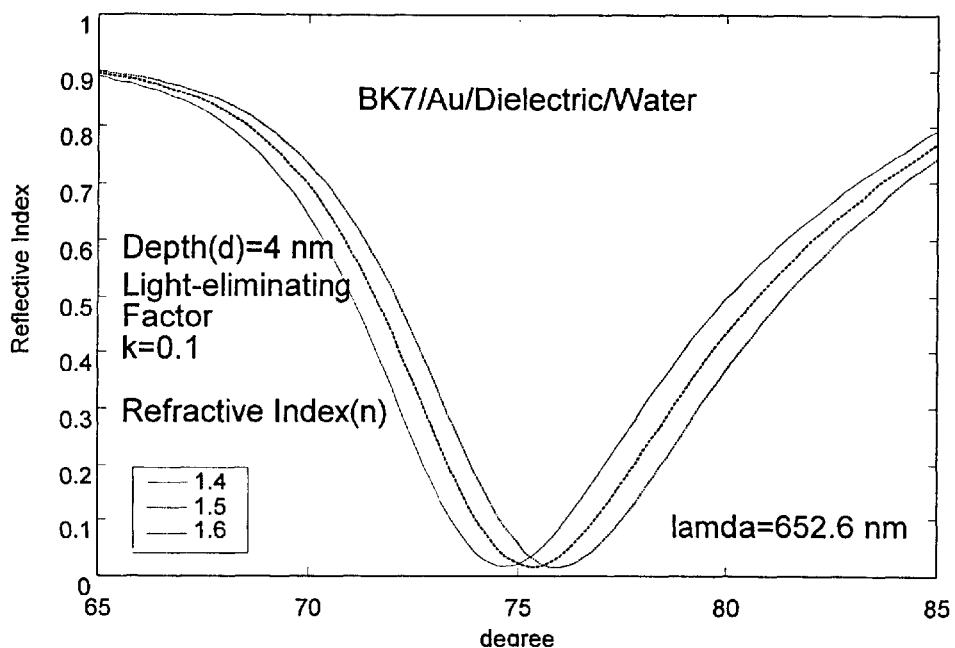
FIG. 6 is a diagram illustrating the frequency spectrum of the surface plasmon resonance (SPR) in dielectric layers with different refractive index according to a preferred embodiment of the present invention.
Figure 7:
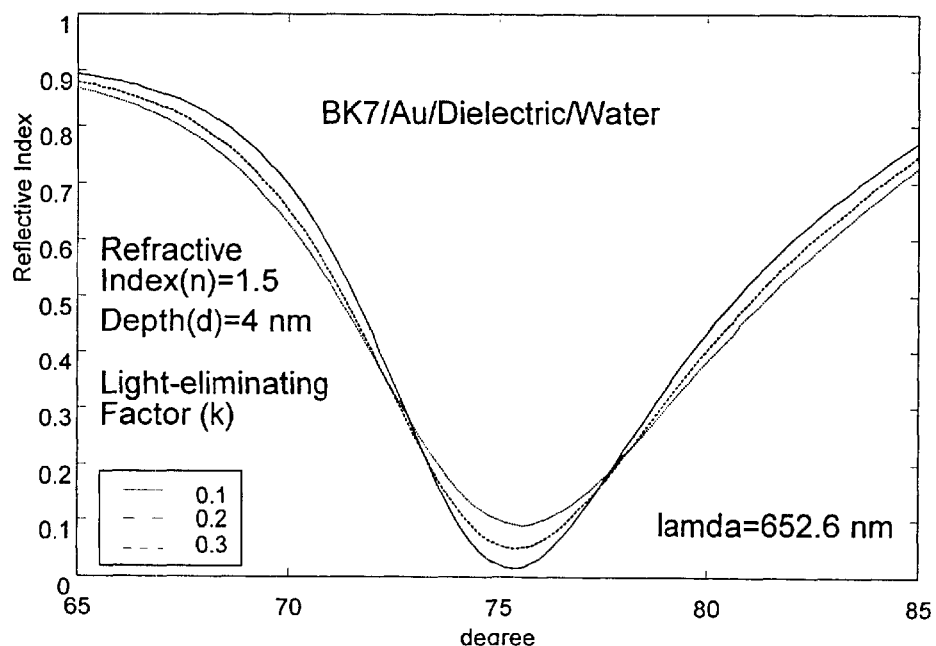
FIG. 7 is a diagram illustrating the frequency spectrum of the surface plasmon resonance (SPR) in dielectric layers with different light-eliminating factor according to a preferred embodiment of the present invention.
Figure 8:
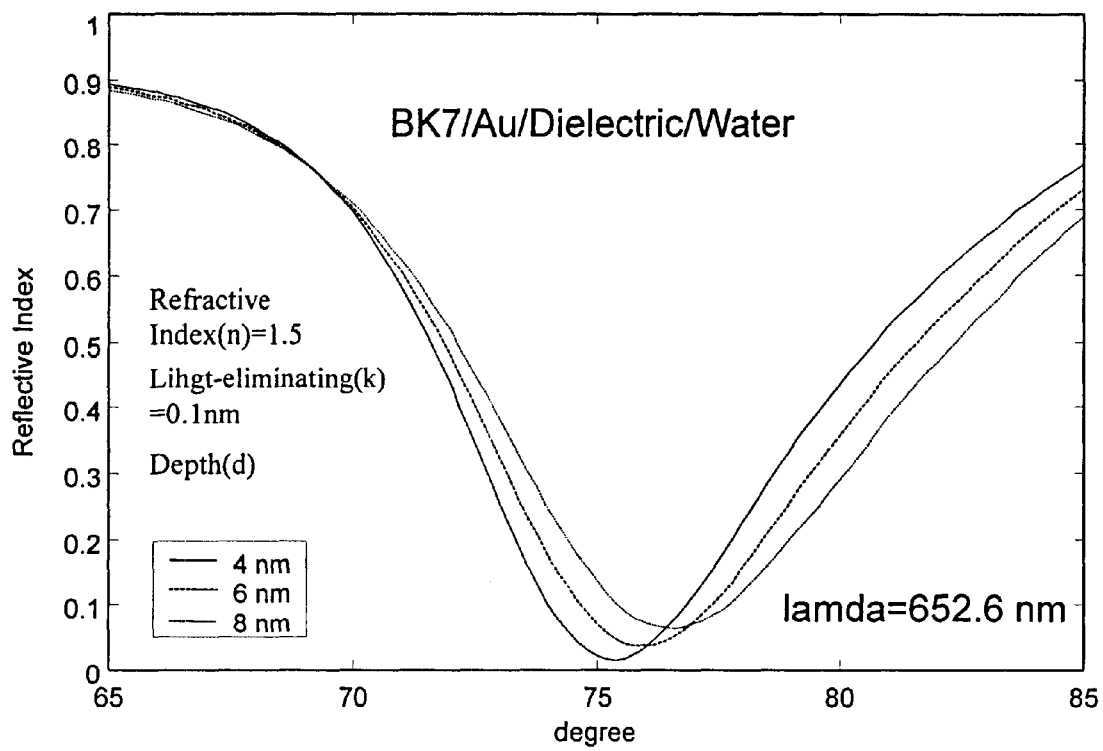
FIG. 8 is a diagram illustrating the frequency spectrum of the surface plasmon resonance (SPR) in dielectric layers with different thicknesses according to a preferred embodiment of the present invention.

Please refer to FIGS. 6–8. The diagrams illustrate the frequency spectra of surface plasmon resonance (SPR) chip in dielectric layers, BK7/Au/Dielectric/Water. FIG. 6 is a diagram illustrating the frequency spectrum of surface plasmon resonance (SPR) in dielectric layers with different refractive index according to a preferred embodiment of the present invention. FIG. 7 is a diagram illustrating the frequency spectrum of surface plasmon resonance (SPR) in dielectric layers with different light-eliminating factor according to a preferred embodiment of the present invention. FIG. 8 is a diagram illustrating the frequency spectrum of surface plasmon resonance (SPR) in dielectric layers with different thicknesses according to a preferred embodiment of the present invention.

From FIGS. 6–8, there are three characteristic values can be found: (a) position, (b) width, and (c) penetrating depth. The change of the resonance position will increase the electric field of the metal-dielectric interface and change the measuring depth. The spectrum curve will sensitively change according to the optical properties of metal and dielectric layers so that the structural and gravity change of the thin dielectric layer can be measured in the present invention. In order to solve the unknown parameters (n, k, and d), the same numbers of the measured values (position, width, and penetrating depth) on the spectrum curve must be measured. The designed dual wavelength ranges in the present invention is used for curvilinearly coordinating spectra. The method of non-linear and a least square is used to mimic the theoretical curve to obtain the parameters. Therefore, the biological molecule (including the liquid thin layer-protein system) can be characterized by the optical parameters.

Figure 9:
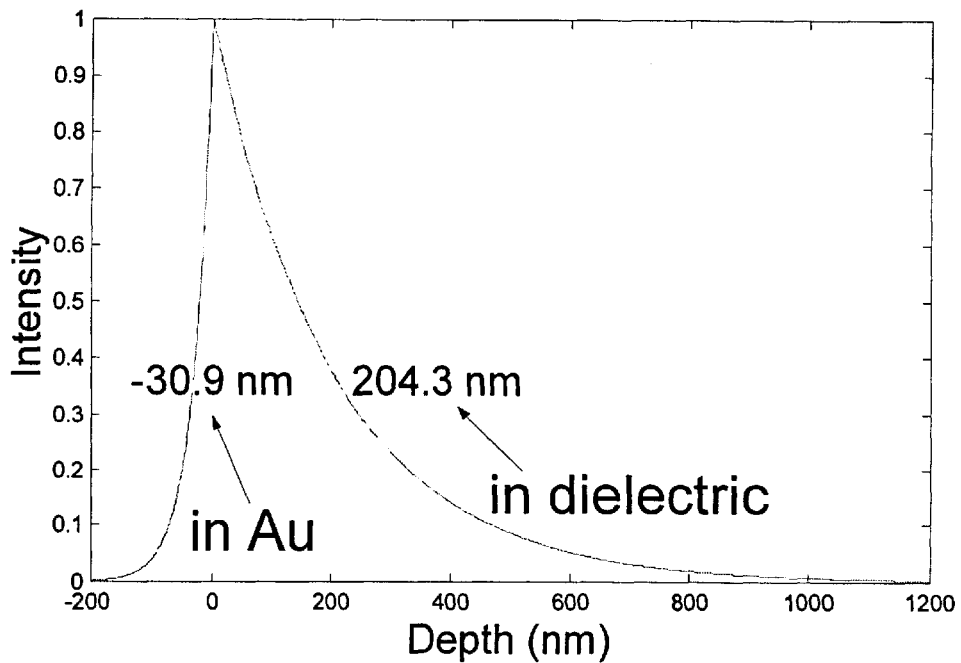
FIG. 9 is a diagram illustrating the penetrating depth within the wavelength range of visible light according to a preferred embodiment of the present invention.
Figure 10:
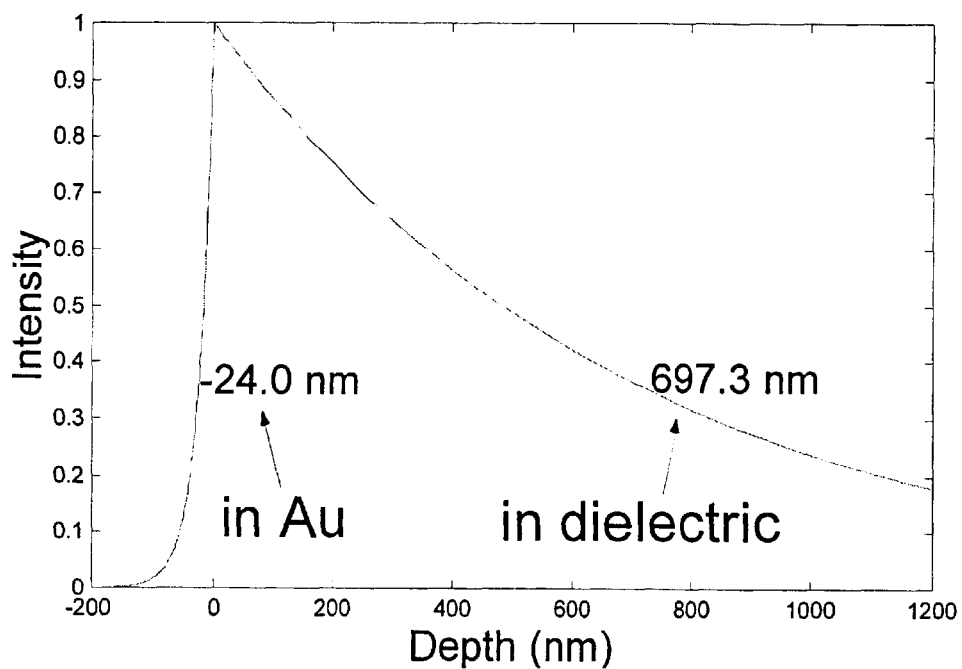
FIG. 10 is a diagram illustrating the penetrating depth within the wavelength range of near infrared light according to a preferred embodiment of the present invention.
Figure 11:
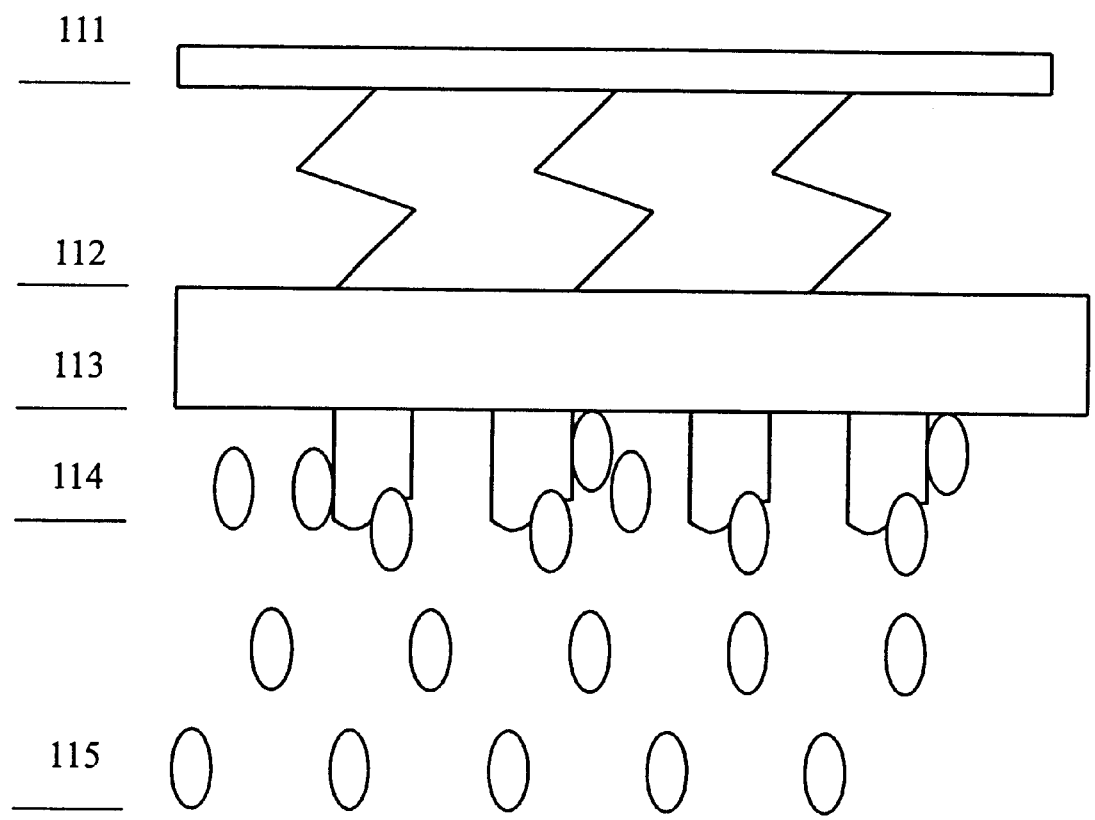
FIG. 11 is a structural diagram illustrating the analysis of the depth of different biological molecules within the wavelength ranges of both visible and near infrared light according to a preferred embodiment of the present invention.
Figure 12:
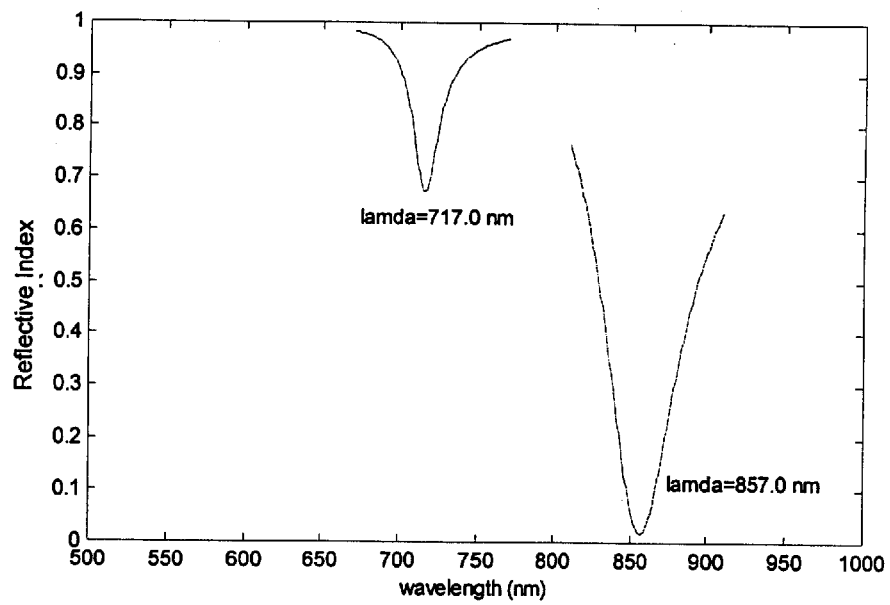
FIG. 12 is a diagram illustrating the average effect of the analytic layer 1 according to a preferred embodiment of the present invention.
Figure 13:
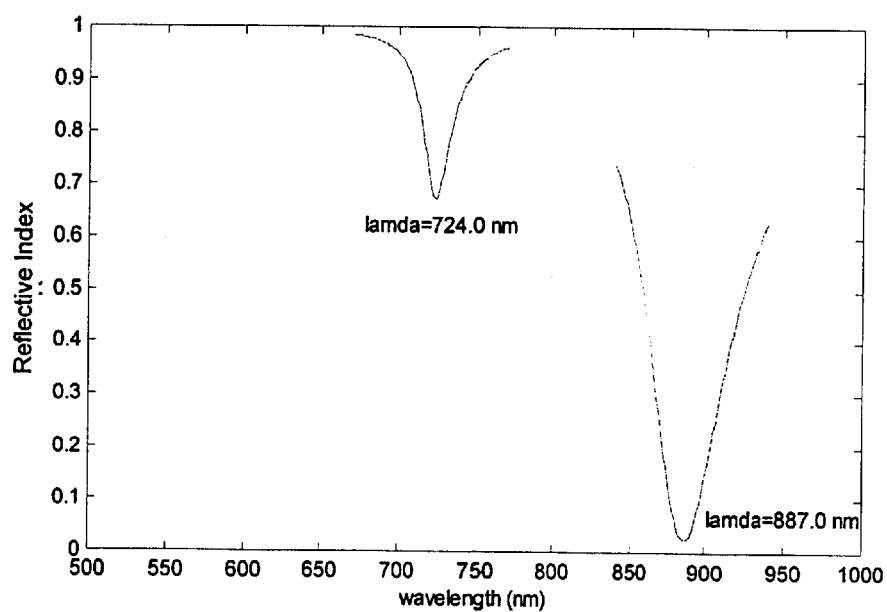
FIG. 13 is a diagram illustrating the average effect of the analytic layer 1 plus analytic layer 2 according to a preferred embodiment of the present invention.

No matter the angle or the wavelength is modulated, the depth difference in Z-axis can not be analyzed three-dimensionally in the present SPR chip. In the present invention, the multi-layer structure designed by the Micro-Electro-Mechanical System (MEMS) is able to accomplish the state of dual resonance. The different depths in Z-axis of biological molecule can be measured by different evanescent fields. Please refer to FIGS. 9 and 10. The diagrams illustrate the penetrating depth within the wavelength range of visible light and near infrared light according to a preferred embodiment of the present invention. FIGS. 9 and 10 show the measured depth of the evanescent wave which is generated by the different resonance wavelength of metal thin layer in the air. FIG. 9 shows that the evanescent wave is able to measure the dielectric layer at a depth of 204.3 nm in the 539.1 nm wavelength of visible light. FIG. 10 shows that the evanescent wave is able to measure the dielectric layer at a depth of 697.3 nm in the 826.6 nm wavelength of near infrared light. This is the main principle of measuring the different depths in Z-axis of biological molecule by evanescent field with different depths. FIG. 11 is a structural diagram illustrating the analyzing of the depth of different biological molecules within the wavelength ranges of both visible and near infrared light according to a preferred embodiment of the present invention. Please refer to FIGS. 12 and 13. The diagrams illustrate the average effect of the analytic layers according to a preferred embodiment of the present invention. The average effect of the molecule in different depths can be analyzed by the generated different resonance wavelength, as shown in FIGS. 12 and 13. By using the Fresnel equation, which is composed of different thin layer thickness, the spectrum position, the depth, and the width in FIGS. 12 and 13 are substituted into the theory for non-linear and a least square cur,linearly coordinating spectra to obtain the two sets of resonance wavelength, the dielectric function, and the thickness. Afterwards, the displacement of the resonance wavelength is considered and removed to obtain the optical properties of the analytic layer 1 plus the analytic layer 2. In a preferred embodiment of the present invention, the multimode metal layer 111, e.g. Au, with an average thickness of 50 nm, the biomedical linker layer 112 with a thickness of 70 nm, and the biomedical ligand layer 113 with a thickness of 20 nm are used for measuring material with different refractive index. When the molecular thin layer 114 (analytic layer 1) has an average thickness of 20 nm, the average refractive index would be 1.37. When the molecular thin layer 115 (analytic layer 2) has an average thickness of 200 nm, the average refractive index would be 1.35.

By using the biomedical sensor system of a surface plasmon resonance (SPR), the properties of biological molecule in Z-axis depth can be analyzed. In addition, a biological detection chip which detects protein sample three-dimensionally by the surface plasmon resonance (SPR) can be provided.

Figure 14A:
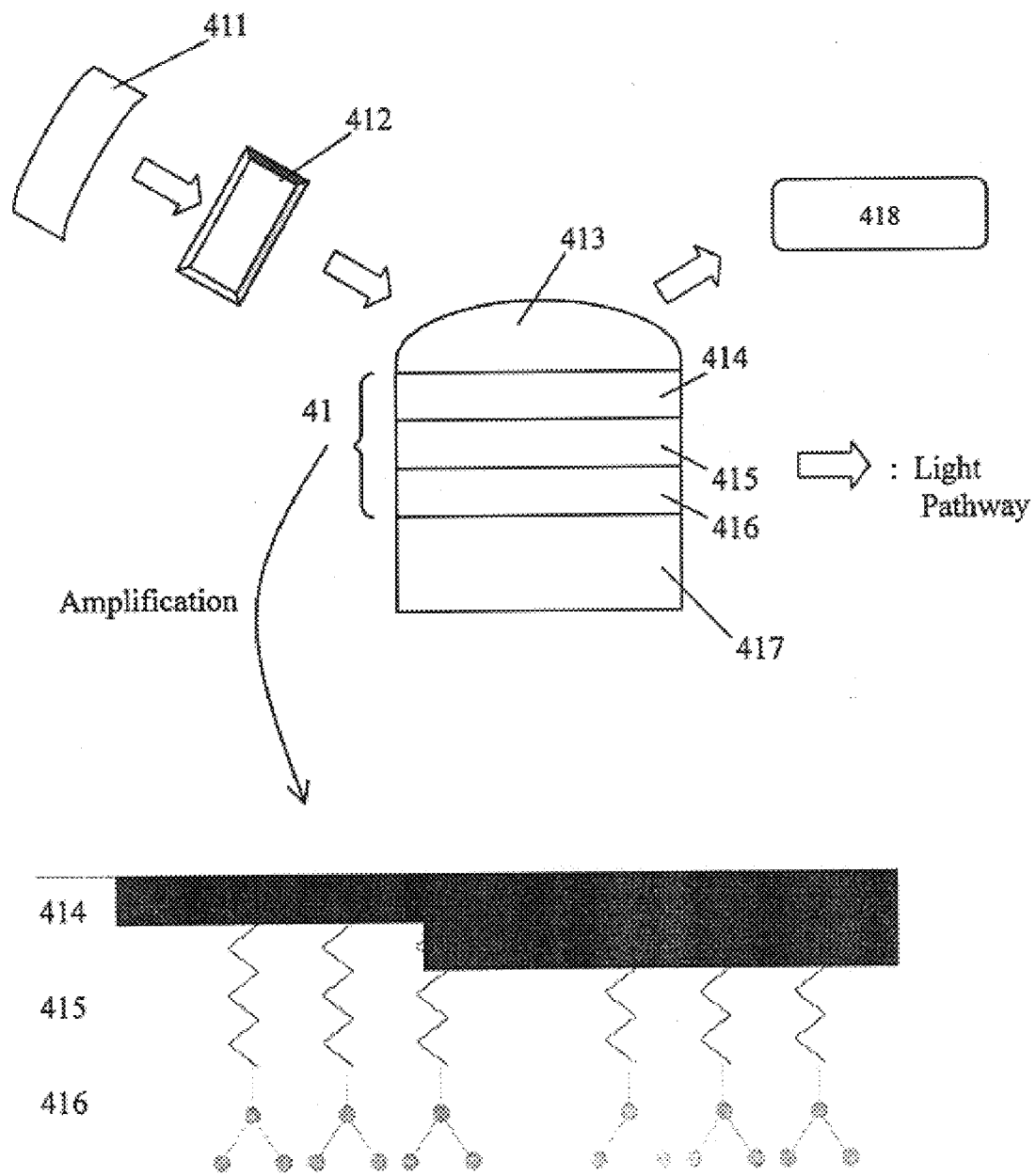
FIG. 14(a) is a diagram illustrating the sensor system of the surface plasmon resonance (SPR) having the function of analyzing molecular depth, which is operated as a form of chip according to a preferred embodiment of the present invention.

In addition, the sensor system of surface plasmon resonance (SPR) can be operated in a chip form, wherein the sensor device of surface plasmon resonance (SPR) has the function of analyzing molecular depth. The main overall arrangement of the elements is shown in FIG. 14(*a*). The light beam of the light source 411 with multi-wavelength is polarized through the polarizer 412 as a p-polarized light. The p-polarized light is then coupled to the surface of the metal thin layer 414 by coupler 413 and a surface plasmon resonance is generated. The chip includes the metal thin layer 414, the biomedical linker layer 415, and the biomedical ligand layer 416. Nevertheless, the substance of interest 417 (analytic solution) is attached under the biomedical ligand layer 416 and the metal thin layer 414 has different thicknesses. If the thickness of the metal thin layer 414 is properly modulated, the resonance wavelength of surface plasmon resonance (SPR) can be generated within the wavelength range of both visible light and near infrared light. Due to the different penetrating depths of evanescent field are generated within the wavelength range of visible light and near infrared light, the reflective spectrum can be analyzed by the spectrograph analyzer 418. The substance of interest 417 of biological molecule is able to be analyzed its different depths. In other words, the ability of three-dimensionally analyzing the depth is accomplished.

Figure 14B:
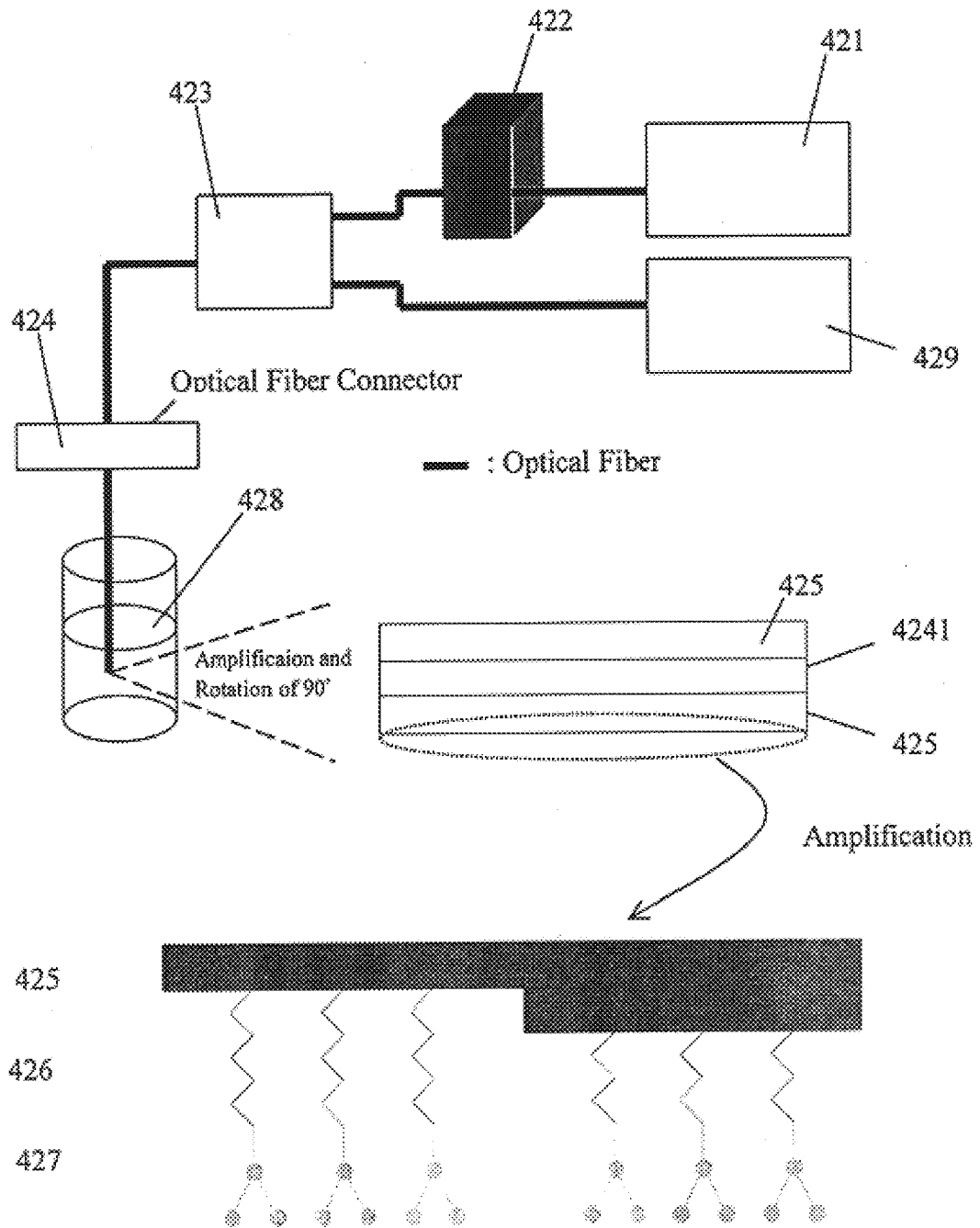
FIG. 14(b) is a diagram illustrating the sensor system of the surface plasmon resonance (SPR) having the function of analyzing molecular depth, which is operated as a form of optical fiber according to a preferred embodiment of the present invention.

In another preferred embodiment of the present invention, the sensor system of surface plasmon resonance (SPR) is operated in a form of optical fiber, wherein the sensor device of surface plasmon resonance (SPR) has the function of analyzing molecular depth. The main overall arrangement of the elements is shown in FIG. 14(b). In this embodiment, the light beam of the light source 421 with multi-wavelength is polarized through the polarizer 422 as a p-polarized light. The p-polarized light is then coupled to the optical fiber form of the sensor device of the surface plasmon resonance (SPR) by the optical fiber connector 424. The metal thin layer 425 with different thicknesses is plated on the axle center 4241 of the optical fiber. The biomedical linker layer 426 and the biomedical ligand layer 427 further cover on the top the metal thin layer 425. If the thickness of the metal thin layer 425 is properly modulated, the resonance wavelength of the surface plasmon resonance (SPR) can be generated within the wavelength range of both visible light and near infrared light. Due to the different penetrating depths of the evanescent field are generated within the wavelength range of visible light and near infrared light, the reflective spectrum can be analyzed by the spectrograph analyzer 419. The substance of interest 428 of biological molecule is able to be analyzed its different depths. In other words, the ability of three-dimensionally analyzing the depth is accomplished.

In conclusion, the sensor system of a surface plasmon resonance (SPR) in the present invention uses the phenomenon of multimode surface plasmon resonance. The differences of the penetrated depth of samples are measured and analyzed by the spectrograph analyzer within the wavelength range of both visible light and near infrared light. Furthermore, the different properties of the biological molecule in different depths after attached on the surface of the metal layer will be measured, including the refractive index, the parameters in dielectric function, the calculated thickness, the surface density, the mass, the volume density, and the uneven depth in the Z-axis. In addition, the characteristics of the present invention includes the polarized light source, light guiding pathway, metal thin layer sensor optical fiber or chip with a thickness of 10–300 nm, the splitter with double channels for visible light and near infrared light, digital signal processing system, and analyzing software. Hence, the present invention is very worthy for industrial development.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A sensor system of a surface plasmon resonance (SPR) for analyzing a characteristic of a substance, comprising:
   an optical device for generating a first light beam and a second light beam in sequence;
   a sensor device mounted between a first dielectric layer and a second dielectric layer for respectively generating a first plasmon wave and a second plasmon wave in response to an optical characteristic change of said first light beam and said second light beam with respective to said substance, wherein said substance is disposed between said sensor device and said second dielectric layer, and a resonance is generated from said first plasmon wave and said second plasmon wave respectively generating a first reflective signal and a second reflective signal in response to a refractive index difference between said first dielectric layer and said second dielectric layer; and
   a measuring device for measuring spectra of said first reflective signal and said second reflective signal and obtaining a measured value, wherein said measured value is substituted into an operational formula to calculate a reference value used for analyzing said characteristic of said substance.

2. The sensor system according to claim 1, wherein said substance is a biological molecule.

3. The sensor system according to claim 1, wherein said substance has a penetrated depth ranged from 1–2500 nm.

4. The sensor system according to claim 1, wherein said first light beam and said second light beam have different wavelengths.

5. The sensor system according to claim 1, wherein said optical device further comprises:
   a light source for generating said first light beam and said second light beam;
   a polarizer for polarizing said first light beam and said second light beam and generating a polarized first light beam and a polarized second light beam,
   plural lens for focusing said polarized first light beam and said polarized second light beam inside an optical fiber so as to allow said polarized first light beam and said polarized second light beam to enter said optical fiber and travel therethrough; and
   a splitter connecting said optical fiber and a spectrometer, wherein said spectrometer is used for analyzing a spectrum change of said first reflective signal and said second reflective signal generated upon said resonance.

6. The sensor system according to claim 1, wherein said first light beam and said second light beam are respectively visible light and near infrared light, wherein said visible light has a wavelength ranged from 400–700 nm and said near infrared light has a wavelength ranged from 700–1500 nm.

7. The sensor system according to claim 1, wherein said sensor device is one of a surface plasmon resonance (SPR) optical fiber sensor and a surface plasmon resonance (SPR) chip sensor.

8. The sensor system according to claim 1, wherein said sensor device further comprises:
   a multi-layer structure; and
   a coupler for coupling said first light beam and said second light beam to said multi-layer structure.

9. The sensor system according to claim 8, wherein said multi-layer structure further comprises a multimode metal layer, a biomedical linker layer and a biomedical ligand layer in sequence.

10. The sensor system according to claim 9, wherein said multimode metal layer has a thickness ranged from 10–300 nm.

11. The sensor system according to claim 9, wherein said multimode metal layer is composed of plural metal layers with different thicknesses.

12. The sensor system according to claim 9, wherein said multimode metal layer is composed of plural metal layers made of different materials.

13. The sensor system according to claim 9, wherein said substance is attached on the surface of said multimode metal layer.

14. The sensor system according to claim 1, wherein said first light beam and said second light beam are incident upon said second dielectric layer through said first dielectric layer.

15. The sensor system according to claim 14, wherein said first dielectric layer has a refractive index larger than that of said second dielectric layer.

16. The sensor system according to claim 1, wherein said measuring device includes a hardware device and a software device.

17. The sensor system according to claim 16, wherein said hardware device is a spectrometer for measuring said measured value and said software device is a digital signal processing program.

18. The sensor system according to claim 1, wherein spectra of said first reflective signal and said second reflective signal have said measured value including a site, a width, and a penetrating depth.

19. The sensor system according to claim 1, wherein said operational formula is a specific equation using a least square curvilinearly coordinating spectra of said first reflective signal and said second reflective signal to obtain said reference value.

20. The sensor system according to claim 1, wherein said reference value includes a refractive index, a light-eliminating factor, and a thickness.

21. A measuring method of a surface plasmon resonance (SPR) system for analyzing a characteristic of a substance, comprising steps of:
   (a) providing a first light beam and a second light beam;
   (b) providing a sensor device for respectively generating a first plasmon wave and a second plasmon wave in response to an optical characteristic change of said first light beam and said second light beam with respect to said substance;
   (c) generating a resonance from said first plasmon wave and said second plasmon wave respectively generating a first reflective signal and a second reflective signal in response to a refractive index difference between a first dielectric layer and a second dielectric layer; and
   (d) measuring spectra of said first reflective signal and said second reflective signal and obtaining a measured value, wherein said measured value is substituted into an operational formula to calculate a reference value used for analyzing said characteristic of said substance.

22. The measuring method according to claim 21, wherein said first light beam and said second light beam are provided from an optical device.

23. The measuring method according to claim 21, wherein said measured value is obtained from a spectrometer.

\* \* \* \* \*